(12) United States Patent
Lieberman et al.

(10) Patent No.: US 10,376,382 B2
(45) Date of Patent: Aug. 13, 2019

(54) METHODS AND APPARATUS FOR FACILITATING A POSTERIOR LUMBAR INTERBODY FUSION PROCEDURE

(71) Applicant: Phoenix Spine Holdings, Inc., Phoenix, AZ (US)

(72) Inventors: Daniel Lieberman, Phoenix, AZ (US); John B. Kinnard, San Tan Valley, AZ (US); Yani Deros, Phoenix, AZ (US)

(73) Assignee: Phoenix Spine Holdings, Inc., Phoenix, AZ (US)

( * ) Notice: Subject to any disclaimer, the term of this patent is extended or adjusted under 35 U.S.C. 154(b) by 246 days.

(21) Appl. No.: 15/353,428

(22) Filed: Nov. 16, 2016

(65) Prior Publication Data

US 2018/0133022 A1    May 17, 2018

(51) Int. Cl.
*A61F 2/46* (2006.01)
*A61F 2/44* (2006.01)
*A61F 2/30* (2006.01)

(52) U.S. Cl.
CPC .............. *A61F 2/447* (2013.01); *A61F 2/442* (2013.01); *A61F 2/4611* (2013.01); *A61F 2002/30426* (2013.01); *A61F 2002/30556* (2013.01); *A61F 2002/30563* (2013.01); *A61F 2002/4475* (2013.01); *A61F 2002/4615* (2013.01); *A61F 2002/4627* (2013.01); *A61F 2002/4628* (2013.01); *A61F 2002/4687* (2013.01)

(58) Field of Classification Search
CPC ........ A61F 2/442; A61F 2/4425; A61F 2/447; A61F 2/4611; A61F 2002/4615; A61F 2002/4475
See application file for complete search history.

(56) References Cited

U.S. PATENT DOCUMENTS

| | | |
|---|---|---|
| 2,112,056 A | 3/1938 | Wappler |
| 3,763,843 A | 10/1973 | Fisher et al. |
| 4,239,296 A | 12/1980 | Kaub |
| 4,624,243 A | 11/1986 | Lowery et al. |
| 4,697,577 A | 10/1987 | Forkner |
| 4,850,342 A | 7/1989 | Hashiguchi et al. |
| 5,554,100 A | 9/1996 | Leiner et al. |

(Continued)

FOREIGN PATENT DOCUMENTS

CN    101669845    3/2010

OTHER PUBLICATIONS

International Search Report, PCT/US17/34341 dated Oct. 6, 2017; 6 pages.

(Continued)

*Primary Examiner* — Samuel S Hanna
(74) *Attorney, Agent, or Firm* — Jennings Strouss & Salmon PLC; Michael K. Kelly; Daniel R. Pote

(57) ABSTRACT

Methods and apparatus for posterior lumbar interbody fusion (PLIF) surgical procedures. The apparatus includes a sleeve assembly for guiding an interbody graft into position between adjacent anatomical structures. The sleeve includes a first piece having a first internal ramp and a second piece having a second internal ramp opposite the first internal ramp, and an elastic band configured to connect the first and second pieces together. The first and second internal ramps comprise a V shape with an opening therebetween through which the interbody graft is urged during the surgical procedure.

3 Claims, 9 Drawing Sheets

(56) References Cited

U.S. PATENT DOCUMENTS

| | | |
|---|---|---|
| 5,569,183 A | 10/1996 | Kieturakis |
| 6,494,881 B1 | 12/2002 | Bales et al. |
| 6,916,286 B2 | 7/2005 | Kazakevich |
| 8,208,995 B2 | 6/2012 | Tearney et al. |
| 8,391,571 B2 | 3/2013 | Cinquin et al. |
| 8,409,080 B2 | 4/2013 | Gumbs et al. |
| 9,687,142 B1 | 6/2017 | Lieberman et al. |
| 2007/0129719 A1 | 6/2007 | Kendale et al. |
| 2009/0187072 A1 | 7/2009 | Manohara |
| 2009/0292361 A1* | 11/2009 | Lopez .................. A61F 2/446 |
| | | 623/17.15 |
| 2010/0324364 A1 | 12/2010 | Sasaki |
| 2012/0016192 A1 | 1/2012 | Jansen et al. |
| 2012/0059470 A1 | 3/2012 | Leiner et al. |
| 2012/0123206 A1 | 5/2012 | Vargas |
| 2012/0130161 A1* | 5/2012 | Lauryssen .......... A61B 17/3439 |
| | | 600/104 |
| 2014/0194683 A1 | 7/2014 | Nakaguchi |
| 2014/0236297 A1* | 8/2014 | Iott ...................... A61F 2/447 |
| | | 623/17.15 |
| 2014/0276015 A1 | 9/2014 | Whiseant |
| 2015/0080973 A1* | 3/2015 | Eastlack ............. A61F 2/4455 |
| | | 606/86 A |
| 2015/0257629 A1 | 9/2015 | Shanninain |
| 2015/0289755 A1 | 10/2015 | Voros et al. |
| 2016/0106551 A1 | 4/2016 | Grimberg et al. |

OTHER PUBLICATIONS

Written Opinion, PCT/US17/34341 dated Oct. 6, 2017; 6 pages.
International Search Report, PCT/US17/62091 dated Feb. 5, 2018; 3 pages.
Written Opinion, PCT/US17/62091 dated Feb. 5, 2018; 8 pages.

\* cited by examiner

METHODS AND APPARATUS FOR FACILITATING A POSTERIOR LUMBAR INTERBODY FUSION PROCEDURE

TECHNICAL FIELD

The present invention relates, generally, to methods and apparatus for facilitating a posterior lumbar interbody fusion (PLIF) procedure and, more particularly, to an expandable device through which an interbody spacer graft may be inserted.

BACKGROUND

Other than the common cold, back pain is the number one reason people visit a doctor in the United States. There are three principle sources of back pain: i) joint pain (40%); ii) pain from a nerve root (40%); and iii) disc pain (20%).

Spinal joint pain occurs in the facet joint between adjacent vertebrae. The five facet joints on each side of the lumbar spine produce pain signals when they become arthritic or because of injury due to trauma, with 90% of cases occurring at the L4/L5 and L5/S1 junctions.

Spinal fusion is a surgical procedure used to correct problems with the small bones in the spine (vertebrae). Adjacent vertebrae are fused together using bone paste so that they heal into a single, solid bone. A posterior lumbar interbody fusion (PLIF) involves adding bone graft to an area of the spine to set up a biological response that causes the bone to grow between the two vertebral elements and thereby preclude articulation at that segment. PLIF promotes spinal fusion by inserting a spacer, also referred to herein as an interbody graft, made of allograft bone and/or a synthetic material (e.g., plastic or titanium) directly into the disc space. When the surgical approach for this type of procedure is from the back it is called a posterior lumbar interbody fusion (PLIF).

In a typical PLIF procedure, the spine is approached through an incision in the midline of the back and the left and right lower back muscles (erector spinae) are stripped off the lamina on both sides and at multiple levels. After the spine is approached, the lamina is removed (laminectomy) which allows visualization of the nerve roots. The facet joints, which are directly over the nerve roots may then be undercut (trimmed) to give the nerve roots more room. The nerve roots are then retracted to one side and the disc space is cleaned of the disc material.

A spacer packed with bone graft material is then inserted into the disc space to promote bone growth between the adjacent vertebrae, allowing them to heal as a single structure.

Presently known endoscopic techniques involve inserting the interbody graft directly into the space between the vertebrae, while holding the nerves and dura out of the way. Specifically, the surgeon screws a handle into the spacer, forces the spacer between the vertebrae and hammers it down to a desired depth, then unscrews and removes the handle from the spacer. This approach is cumbersome, and tends to irritate to the surrounding nerves and dura.

Methods and apparatus are thus needed which overcome these and other limitations of the prior art.

Various features and characteristics will also become apparent from the subsequent detailed description and the appended claims, taken in conjunction with the accompanying drawings and this background section.

BRIEF SUMMARY

Various embodiments of the present invention relate to methods and apparatus for, inter alia: i) a device for controllably guiding the interbody graft into the space between adjacent vertebrae to thereby avoid damaging nearby spinal nerves during insertion of the interbody graft; ii) an expandable sleeve having opposing ramped internal surfaces urged together by an elastomeric band, configured such that downward force applied to the interbody graft causes the ramps to move apart, allowing the graft to slide through the sleeve and into place between adjacent vertebrae; iii) a method for first inserting the guide sleeve into the space between adjacent vertebrae, and thereafter pushing the interbody graft structure downwardly through the sleeve; iv) a tool for inserting the guide sleeve into place between the vertebrae, and for removing the sleeve after the interbody graft has been inserted into the space between the vertebrae; v) a locking mechanism which allows the surgeon to selectively lock and unlock the insertion tool to the guide sleeve; vi) a guide sleeve including transverse ramps to facilitate inserting the interbody graft at an angle; and vii) a technique for 3D printing the guide sleeve based on a radiological scan of the surgical environment to thereby customize the sleeve to the particular patient anatomy.

It should be noted that the various inventions described herein, while illustrated in the context of a posterior lumbar interbody fusion (PLIF) procedure, are not so limited. Those skilled in the art will appreciate that the inventions described herein may contemplate any procedure in which it is desired to insert a spacer between adjacent anatomical surfaces.

Various other embodiments, aspects, and features are described in greater detail below.

BRIEF DESCRIPTION OF THE DRAWING FIGURES

Exemplary embodiments will hereinafter be described in conjunction with the following drawing figures, wherein like numerals denote like elements, and:

DETAILED DESCRIPTION OF PREFERRED EXEMPLARY EMBODIMENTS

Figure 1:
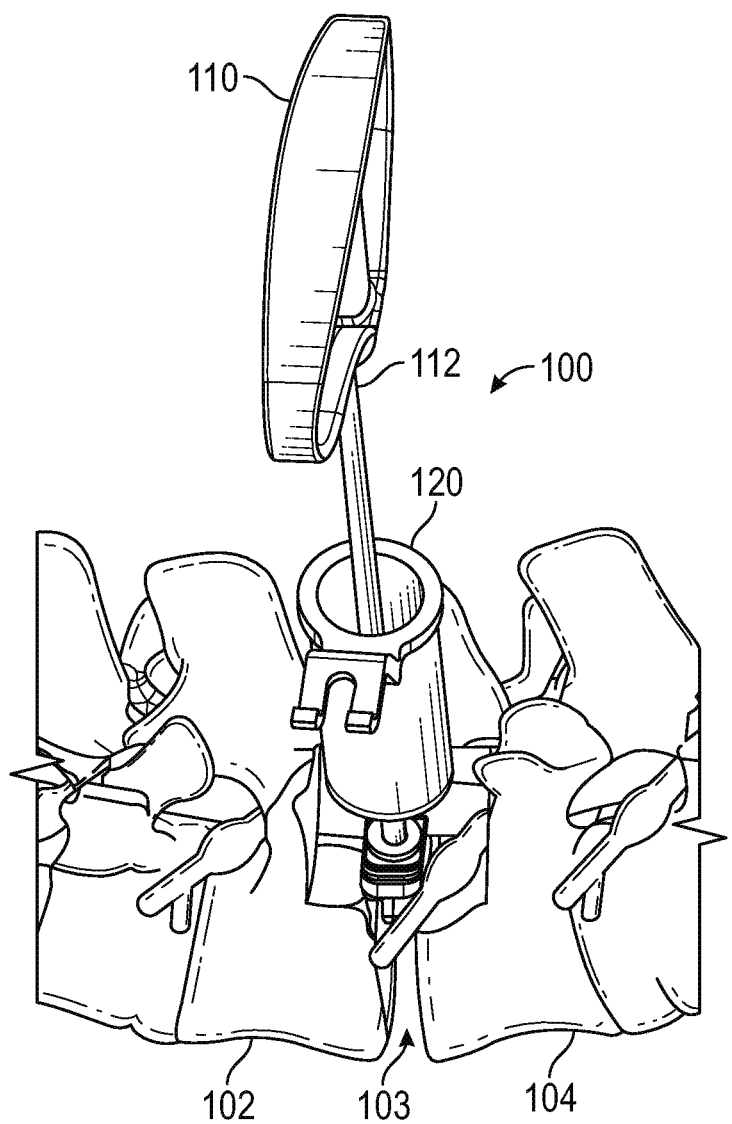
FIG. 1 is a schematic perspective view of a hand tool extending through a retractor tube to place an exemplary ramped guide sleeve between adjacent vertebrae for use in performing a posterior lumbar interbody fusion (PLIF) surgical procedure in accordance with various embodiments.

The following detailed description of the invention is merely exemplary in nature and is not intended to limit the invention or the application and uses of the invention. Furthermore, there is no intention to be bound by any theory presented in the preceding background or the following detailed description.

Various embodiments of the present invention relate to devices and associated methods for performing medical procedures, including but not limited to posterior lumbar interbody fusions (PLIF), in which a spacer or insert such as an interbody graft is placed between anatomical structures (e.g., adjacent vertebrae).

By way of brief introduction, presently known PLIF procedures insert the spacer directly into the space between vertebrae, which can inadvertently pinch, lacerate, or otherwise adversely affect nearby nerve tissue. By using the ramped guide sleeve of the present invention, the spacer may be urged through the guide sleeve and into the region between the vertebrae while avoiding contact with nerve tissue in the surrounding environment.

In an embodiment, a hand tool is inserted into the guide sleeve and turned 90 degrees to lock the guide sleeve to the end of the hand tool. The distal end (bottom) of the guide sleeve has a lateral dimension (e.g., on the order of 2 to 10 millimeters) configured to snugly fit into the space between adjacent vertebrae from which disc tissue was previously removed. Once the guide sleeve is in place, the hand tool is turned 90 degrees to unlock it from the sleeve and removed. A second hand tool (or, alternatively, the same tool) is then used to maneuver the interbody graft (spacer) into engagement with the guide sleeve. The tool is then used to push the spacer through the guide sleeve and into place between the vertebrae, and the surrounding area packed with bone paste. The tool used to install the insert is then removed, and the first tool re-inserted into the guide sleeve and turned 90 degrees to lock the end of the tool into engagement with the guide sleeve. The guide sleeve is then removed from the patient, completing the procedure.

In an embodiment, the guide sleeve comprises a pair of mating pieces held together by an elastomeric band. Each mating piece includes a downwardly extending internal ramp surface. As the insert is pushed downwardly through the guide sleeve against the ramped surfaces, the mating pieces are urged away from each other, gradually increasing the separation between the adjacent vertebrae. At the same time, the insert travels through the guide sleeve and into place at a desired depth between the vertebrae. Once the insert is pushed all the way out through the bottom of the guide sleeve, the elastomeric band urges the mating pieces back together to facilitate subsequent removal of the sleeve, as described in greater detail below.

In an alternate embodiment, the guide sleeve includes—in addition to the foregoing ramped surfaces—an inclined transverse channel configured to guide the insert into the space between the vertebrae at an angle with respect to the longitudinal axis of the sleeve.

In accordance with yet a further aspect of the invention, a digital image (e.g., a CT scan) of the site at which the guide sleeve is to be placed is used to render a 3D model of the external configuration of the guide sleeve, and the model used to 3D print the guide sleeve at or near the surgical site. In this way, the guide sleeve will precisely fit into position between the vertebrae, specifically customized to the surgical environment.

Referring now to FIG. 1, an assembly 100 for removably lodging a guide sleeve into the space 103 between adjacent vertebrae 102, 104 comprises a hand tool having a handle 110 and a shaft 112, and a retractor tube 120.

Figure 2:
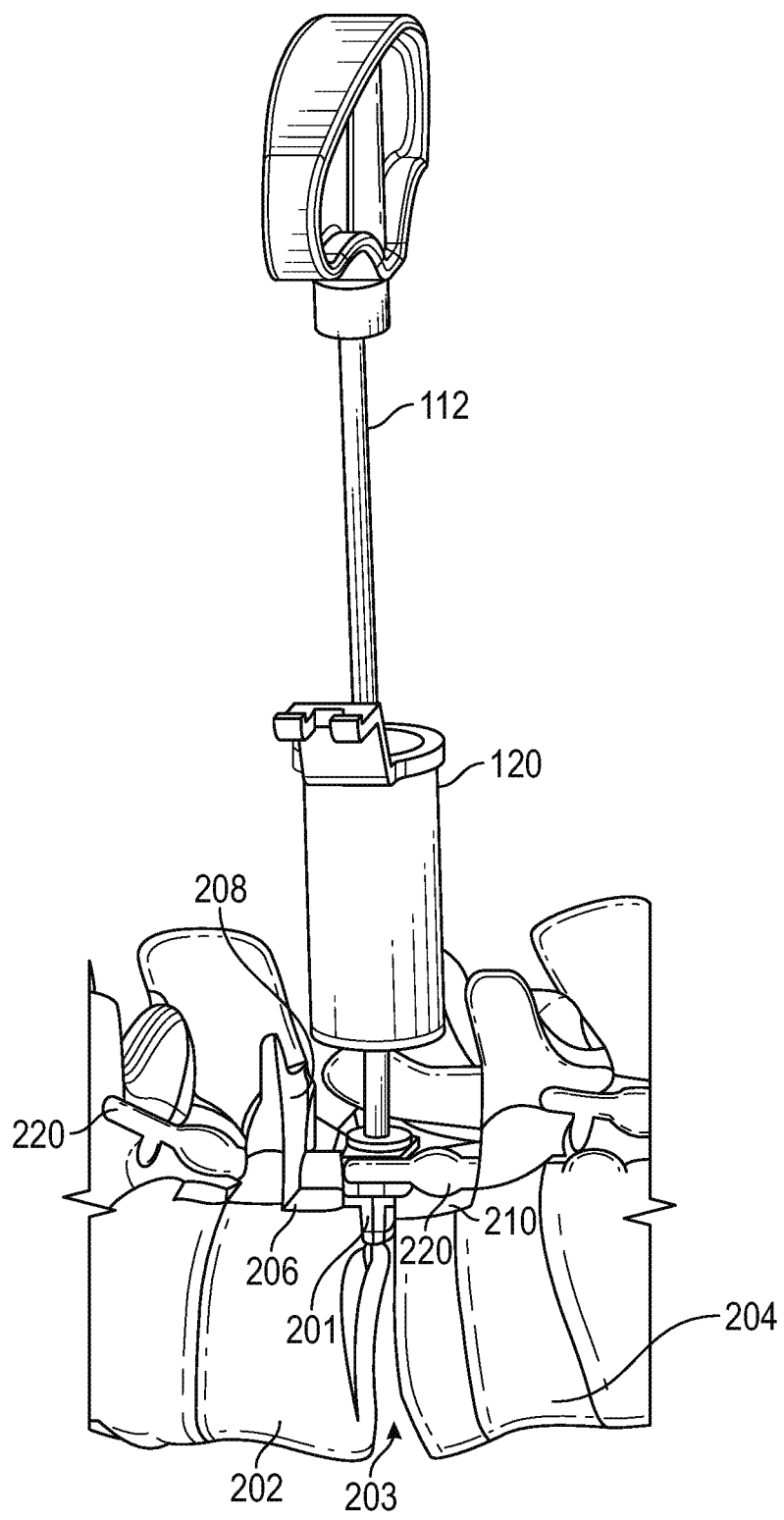
FIG. 2 is a schematic front elevation view of the components shown in FIG. 1, illustrating ledges prepared on opposing vertebrae upon which corresponding shoulders of an exemplary guide sleeve are positioned in accordance with various embodiments.

FIG. 2 illustrates the surgical site at which the guide sleeve 201 is installed. More particularly, a space 203 is created between respective vertebrae 202, 204 after the disc material is removed, as is known in the art. A first seat surface (or ledge) 206 and a first back surface 208 are drilled, milled, or otherwise cut into a portion of vertebra 202, and a second seat surface 210 and a second back surface (not visible in FIG. 2) is similarly formed in vertebra 204. Those skilled in the art will appreciate that some version of these anatomical surfaces may occur naturally, such that the surgeon may either use the surfaces as they exist or adapt them to accommodate the guide sleeve of the present invention, as desired. In accordance with various embodiments, using the guide sleeve of the present invention to guide the interbody graft (discussed below) into the space 203 avoids (or at least reduces) potential damage to nerve tissue 220 as the graft passes between the vertebrae and into position.

Figure 3:
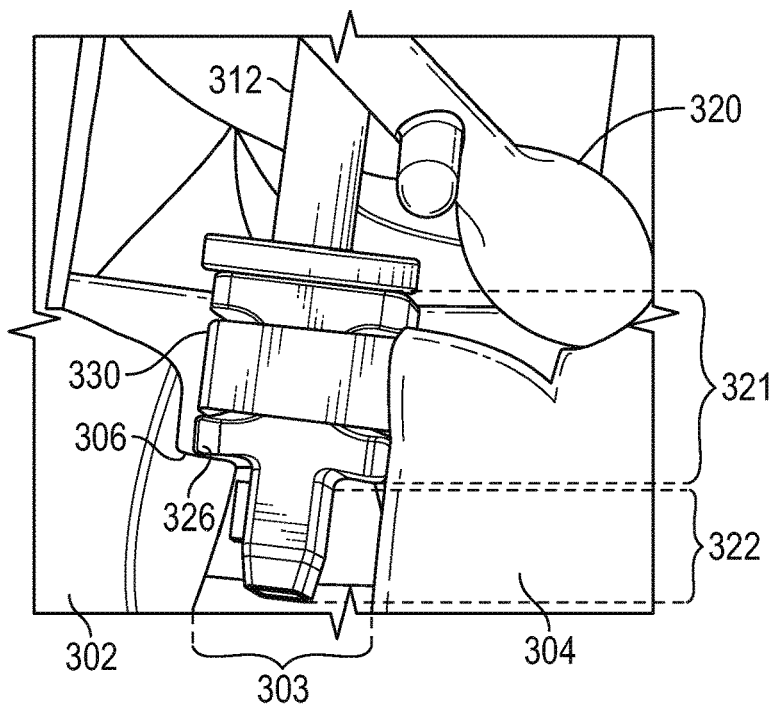
FIG. 3 is a close-up perspective view of a shoulder of an exemplary guide sleeve resting on a vertebral bone ledge in accordance with various embodiments.

Referring now to FIG. 3, a first vertebra 302 includes a ledge 306 and, depending on the surgeon's judgement, a similar ledge may also be formed in a second vertebra 304. An exemplary guide sleeve includes a body portion 321 terminating at a shoulder 326, an elastic band 330, and a shank portion 322 extending downwardly from the body. As described in greater detail below, the body portion 321 comprises mating halves, each having an internal ramp. After first moving nerve tissue 320 out of the way, the guide sleeve is secured to the end of the tool shaft 312, and maneuvered into position such that the shank portion 322 extends into the space 303 between the vertebrae, and the shoulder 326 abuts the ledge 306.

Figure 4:
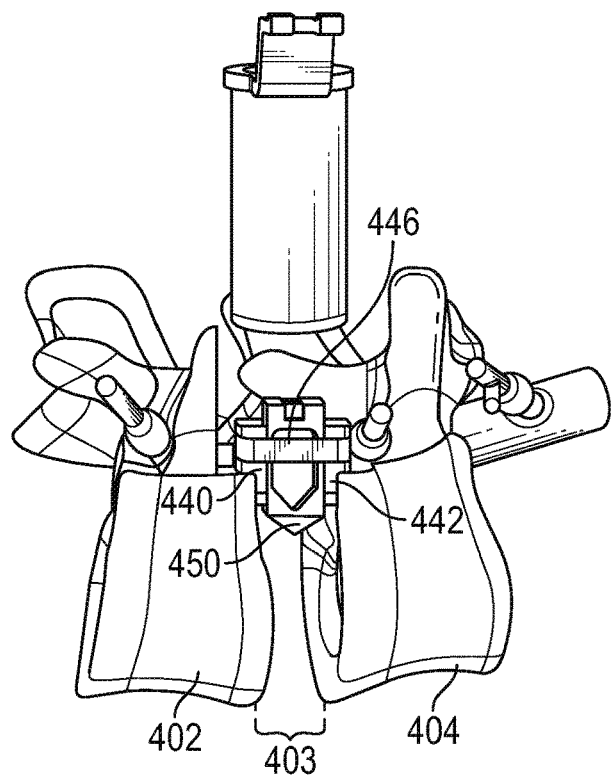
FIG. 4 is a perspective view of an interbody graft (also referred to herein as an insert) extending through an exemplary guide sleeve and into position between adjacent vertebrae in accordance with various embodiments.

FIG. 4 shows an interbody graft 450 (also referred to herein as a spacer or insert) extending through an exemplary guide sleeve and into the region 403 between adjacent vertebrae 402, 404. In the illustrated embodiment, the guide sleeve includes a first piece 440 resting on a ledge of vertebra 402, and a second opposing piece 442 resting on an opposing ledge of vertebra 404. A band 446 suitably urges the first and second pieces 440, 442 together. In the position shown in FIG. 4, the graft 450 has pushed the opposing pieces 440, 442 away from each other through the interaction between the graft 450 and the internal ramps (not shown in FIG. 4), thereby urging vertebrae 402 and 404 away from each other to allow the graft 450 to be permanently inserted therebetween.

Figure 5:
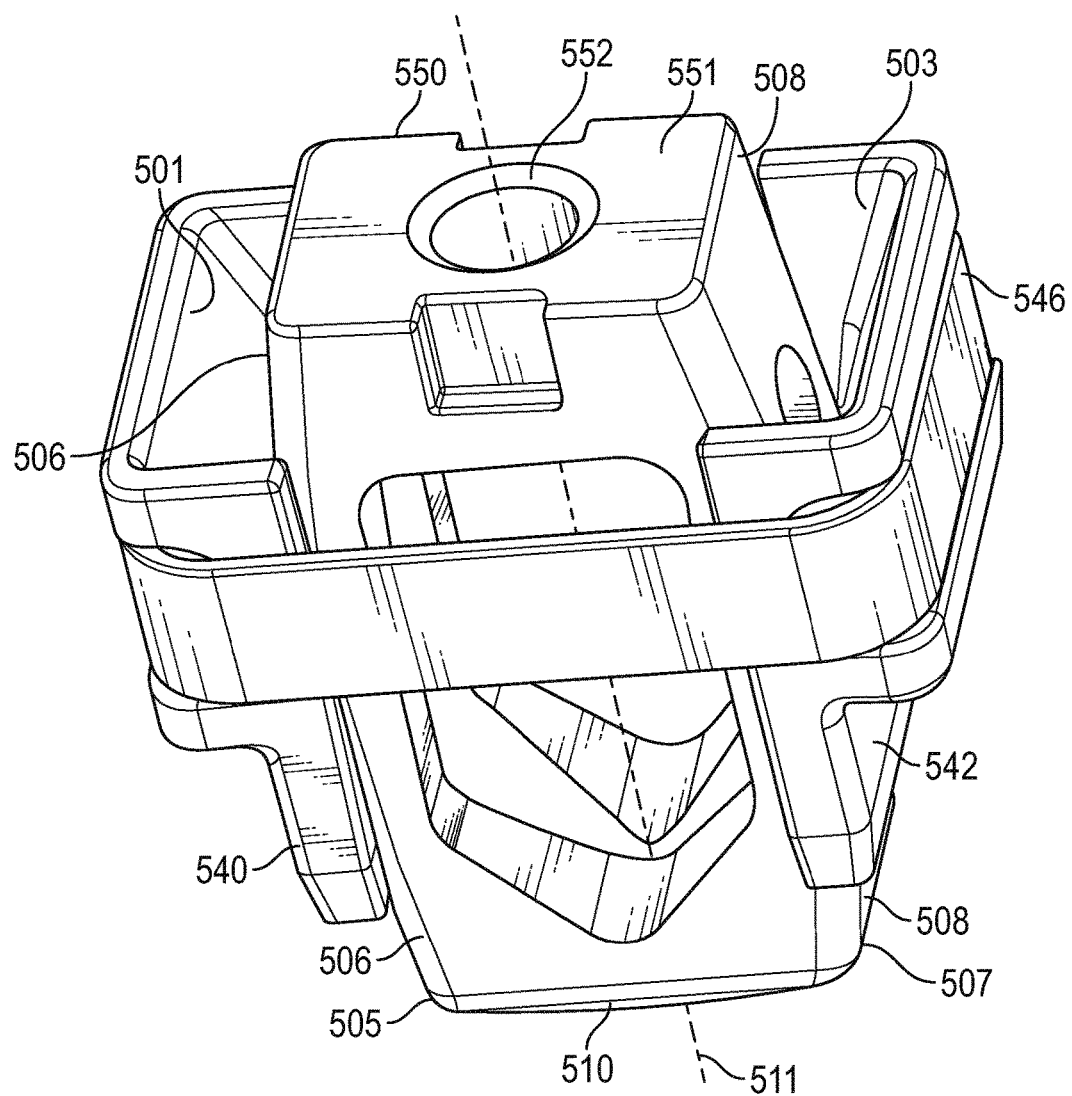
FIG. 5 is a close-up perspective view of an exemplary guide sleeve shown in the extended position as a result of the insert having pushed the opposing pieces of the sleeve apart through the interaction of the insert with the ramped internal surfaces of the guide pieces in accordance with various embodiments.

FIG. 5 shows a close-up perspective view of an exemplary guide sleeve 550 in the extended position as a result of the interbody graft having pushed the opposing pieces of the sleeve apart. In particular, the graft 550 comprises a top surface 551 through which a threaded hole 552 extends for removably receiving a threaded end of an installation tool. Those skilled in the art will appreciate that any type of mechanism may be employed to releasably secure the graft to the installation tool, as desired. The graft 550 further includes a left side surface 506 (not visible in FIG. 5), a right side surface 508, a bottom surface 510 (not visible), a left bottom edge 505 spanning the junction between the left surface 506 and the bottom surface 510, and a second bottom edge 507 spanning the junction between the right surface 508 and the bottom surface.

With continued reference to FIG. 5, the guide sleeve 550 includes a first piece 540 and a second piece 542 held together by a band 546. The first piece 540 includes a ramp surface 501, and the second piece 542 includes an opposing ramp surface 503. As the graft 550 is pushed downwardly along its longitudinal axis 511, the left bottom edge 505 slides along ramp 501 urging first piece 540 to the left, and the right bottom edge 507 slides along ramp 503 urging second piece 542 to the right pushing their corresponding vertebrae away from each other and increasing the space between them to thereby allow the graft 550 to be placed into the resulting space to a desired depth. With momentary reference to FIG. 6, the graft 650 is pushed through the bottom of the guide sleeve (between respective pieces 640, 642), and into place between the vertebrae.

Figure 7:
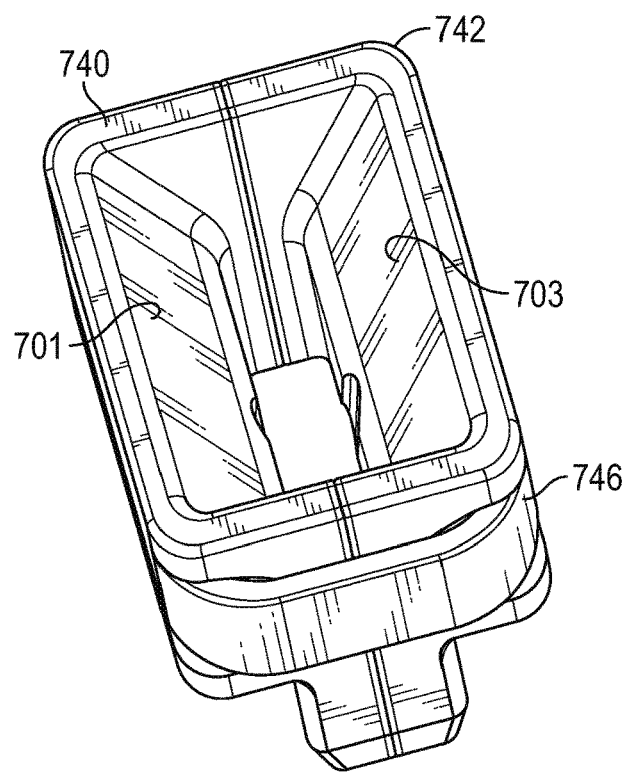
FIG. 7 is a schematic perspective view of the top of an exemplary guide sleeve, with the opposing internal ramped surfaces in the retracted position after the insert has been pushed all the way through and out the bottom of the guide sleeve in accordance with various embodiments.
Figure 8:
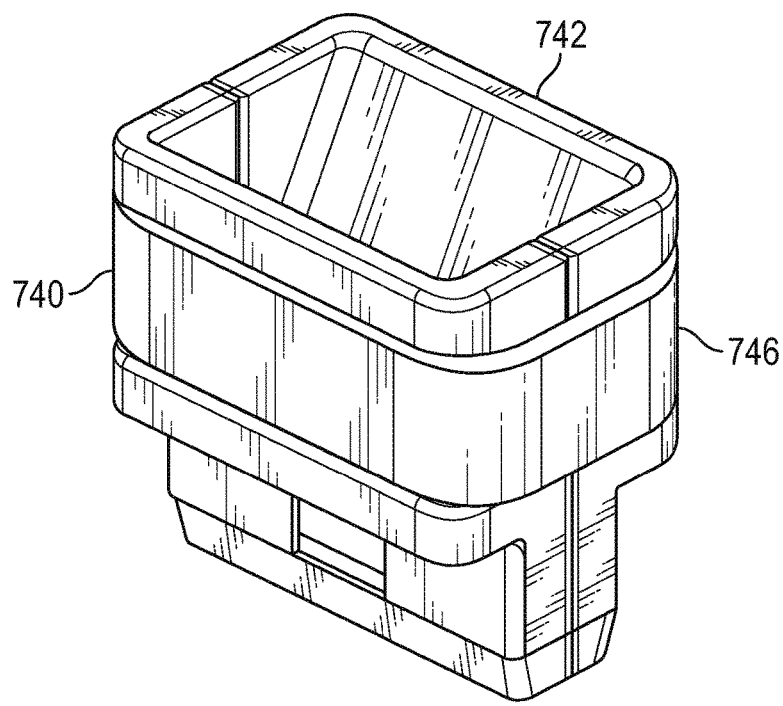
FIG. 8 is a schematic perspective view of the guide sleeve of FIG. 7 in accordance with various embodiments.

Referring now to FIGS. 7 and 8, once the graft is pushed out through the bottom of the guide sleeve, the guide sleeve collapses back to its closed configuration. Specifically, the elastomeric band 746 pulls the first piece 740 (including ramp 701) and second piece 742 (including ramp 703) together, allowing the sleeve to be removed as described below.

Figure 6:
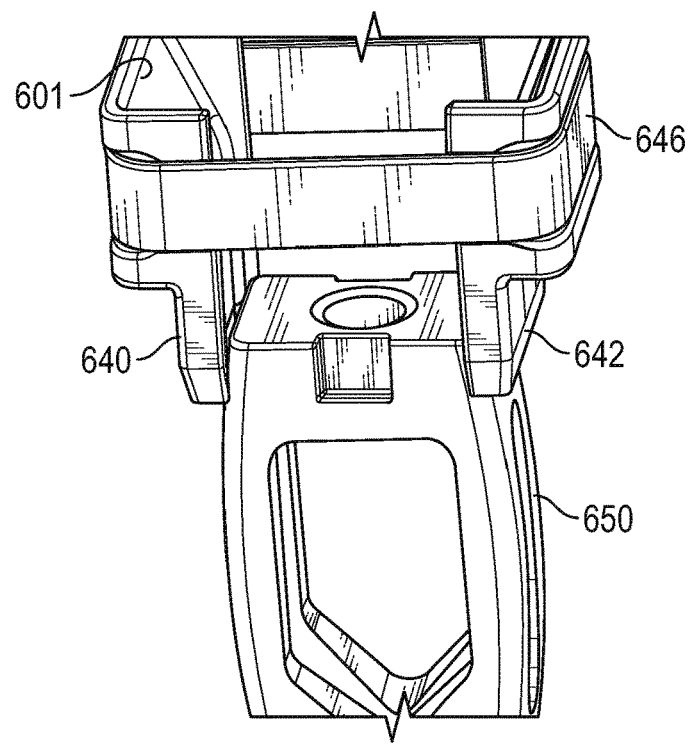
FIG. 6 is a perspective view of the guide sleeve and insert of FIG. 5, showing the insert extending nearly fully downwardly through the guide sleeve in accordance with various embodiments.
Figure 9:
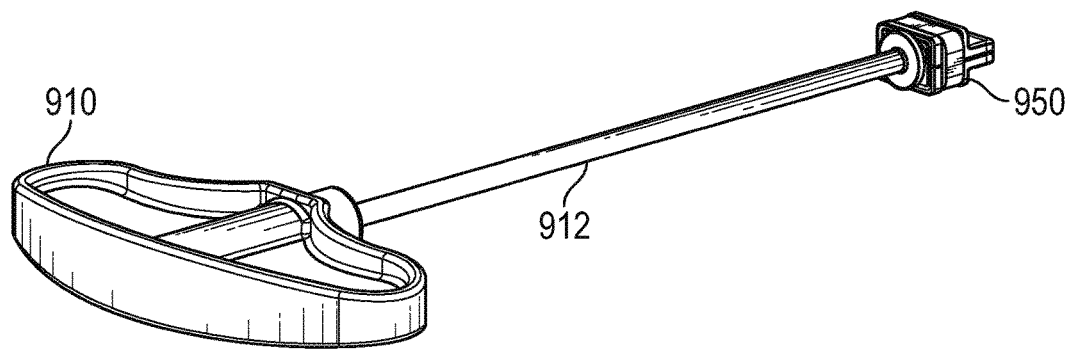
FIG. 9 is a perspective view of an exemplary hand tool and guide sleeve assembly in accordance with various embodiments.
Figure 10:
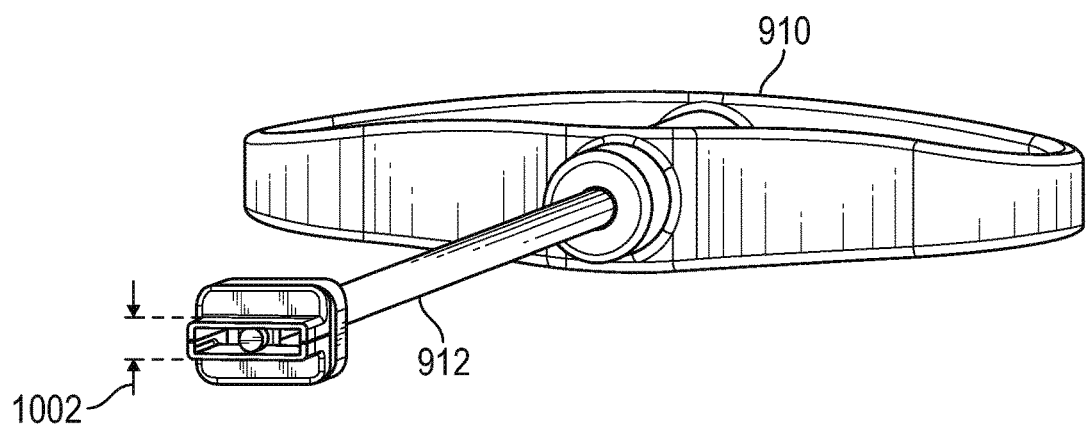
FIG. 10 is a perspective view of the assembly of FIG. 9, illustrating the bottom of the guide sleeve in accordance with various embodiments.

With reference to FIGS. 9 and 10, an exemplary hand tool and guide sleeve assembly includes a handle 91o, a tool shaft 912, and a ramped guide sleeve 950 releasably secured to the distal end of the shaft. As best seen in FIG. 10, the shank portion of the guide sleeve is characterized by a thickness dimension 1002 configured to fit within the anatomical structures between which the sleeve is intended to be placed. In the context of an adult PLIF procedure, the initial separation between the adjacent vertebrae is in the range of 2 to 8 mm, and preferably about 6 mm. when fully expanded (as shown in FIG. 6, this dimension is configured to match the desired separation to be imparted to the adjacent anatomical structures. For an adult PLIF procedure, the final separation is suitably in the range of 10 to 20 mm, and preferably about 14 to 16 mm.

Figure 11:
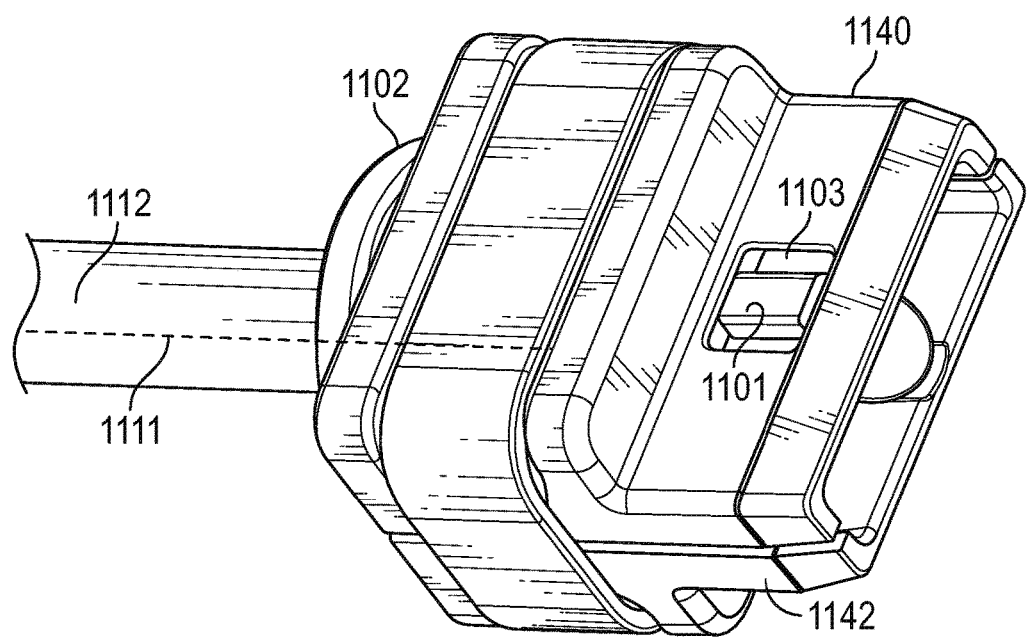
FIG. 11 is a close up perspective view of an exemplary locking mechanism for releasably securing the guide sleeve to the distal end of the hand tool in accordance with various embodiments.
Figure 12:
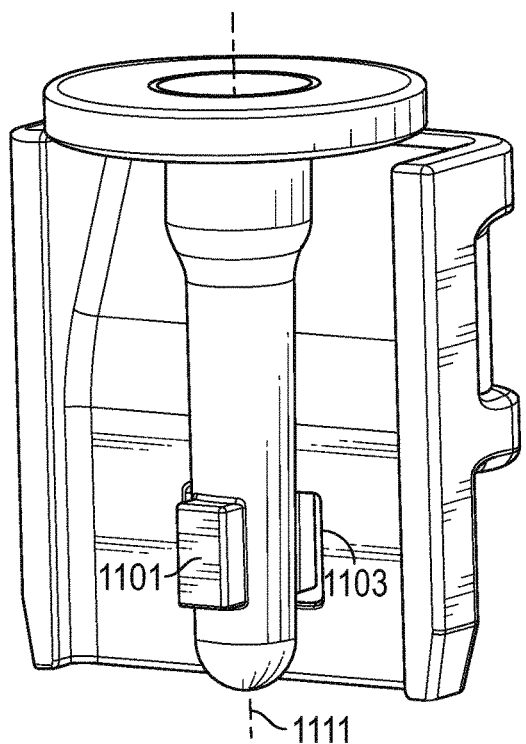
FIG. 12 is a partial cut-away view of the assembly of FIG. 11, showing the locking mechanism in the locked position in accordance with various embodiments.

The manner in which the guide sleeve is locked and unlocked into and out of engagement with the installation tool will now be described in conjunction with FIGS. 11 and 12.

More particularly, an exemplary locking mechanism for releasably securing the guide sleeve to the distal end of the hand tool suitably includes a pair of tabs 1101 extending radially from the distal end of the shaft 1112, and a corresponding pair of slots 1103 formed within the shank portion of each opposing guide piece 1140, 1142. At the angular orientation shown in FIGS. 11 and 12, the tabs 1101 extend through the slots 1103, locking the guide sleeve to the installation tool for placing the sleeve between the vertebrae and removing the sleeve from the site. To unlock the tool from the sleeve, the handle 1112 may be rotated 90 degrees about the shaft axis 1111 to remove the tabs from the slots, allowing the tool to be inserted into and removed from the sleeve as needed.

Figure 13:
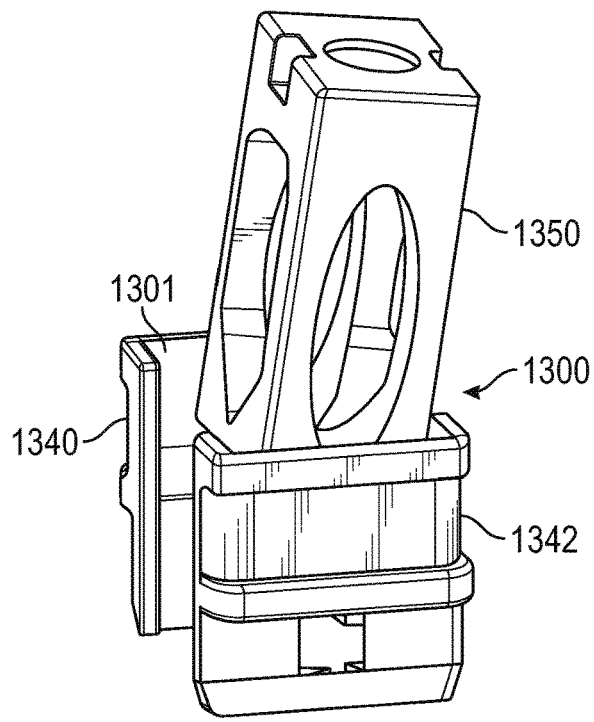
FIG. 13 is a schematic perspective view of an alternate embodiment of a guide sleeve having transverse inclined surfaces in addition to the opposing ramp surfaces, showing an insert near the beginning of its travel through the guide sleeve in accordance with various embodiments.
Figure 14:
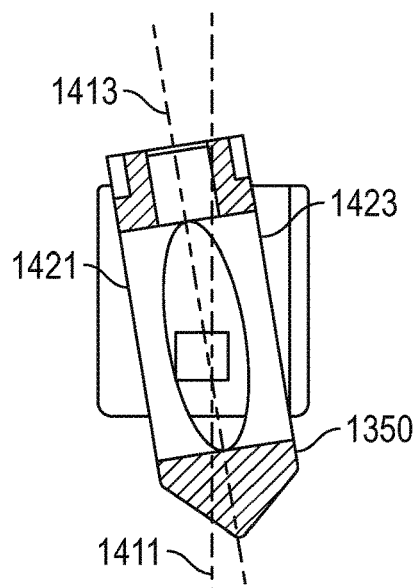
FIG. 14 is a cross-section view of the assembly of FIG. 13, showing the insert mid-way through the guide sleeve in accordance with various embodiments.
Figure 15:
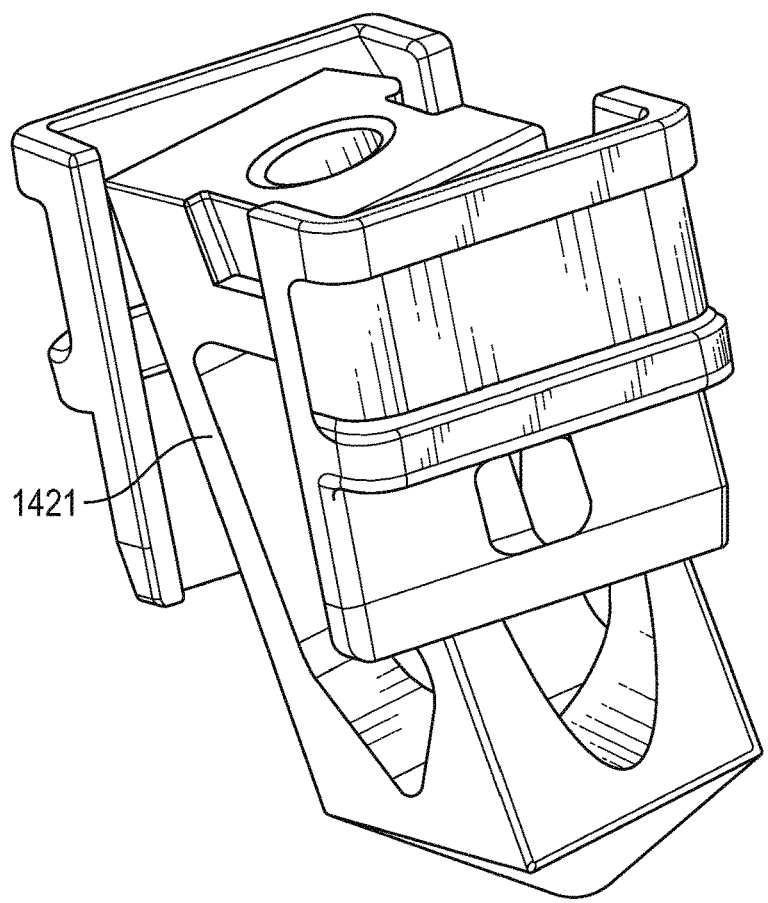
FIG. 15 is a schematic perspective view of the assembly of FIGS. 13 and 14, showing the insert further extending through the guide sleeve in accordance with various embodiments.

An alternate embodiment in which the graft may be inserted into the space between the vertebrae along an arcuate path will now be described in conjunction with FIGS. 13-15.

More particularly, a guide sleeve 1300 includes a first piece 1340 having a first ramp 1301 and a second piece 1342 having an opposing ramp (not visible in FIG. 13), as generally described above. In addition, the sleeve includes transverse internal surfaces configured to guide the graft 1350 along a path at an angle relative to the longitudinal axis of the sleeve as the graft passes through the sleeve. In particular and with momentary reference to FIG. 14, the sleeve may be characterized by a longitudinal axis 1411, with transverse inclined surfaces 1421, 1423 configured to guide the graft 1350 along a path defined by axis 1413 which is inclined at an angle relative to axis 1411. In this way, the graft may be installed into place even if the anatomical structures do not conveniently allow for direct insertion along a straight line defined by the longitudinal axis of the guide sleeve.

In a further embodiment, the guide sleeve may be fabricated to precisely match the patient's anatomy. For example, the guide sleeve may be printed using a 3D printer based on a radiological scan of the surgical environment.

A sleeve assembly is thus provided for guiding an interbody graft into position between adjacent anatomical structures during a surgical procedure. The assembly includes: a first piece having a first internal ramp; a second piece having a second internal ramp disposed opposite the first internal ramp; and an elastic band configured to urge the first and second pieces together. The first and second internal ramps comprise a V shape with an opening therebetween through which the interbody graft travels during the surgical procedure.

In an embodiment, the first and second pieces are configured to: i) mate with each other in a closed position; and separate from each other in an extended position.

In an embodiment, the first piece comprises a first body portion and a first shank portion extending from the first body portion, and the second piece comprises a second body portion and a second shank portion extending from the second body portion.

In an embodiment, the distal ends of the first and second shank portions are configured to be removably inserted between the anatomical structures.

In an embodiment, the surgical procedure comprises a lumbar inter-body fusion, the anatomical structures comprise adjacent vertebrae, and the distal ends of the first and second shank portions comprise a combined width dimension in the range of 2 to 8 mm.

In an embodiment, the assembly further includes a locking mechanism configured to releasably secure the assembly to an installation tool.

In an embodiment, the locking mechanism comprises a slot formed in at lease on of the first and second pieces, the slot configured to selectively receive a tab extending radially from a shaft of the installation tool.

In an embodiment, the first and second ramps are configured to urge the first and second pieces away from each other in response to downward force applied to the ramps by the interbody graft; and the band is configured urge the first and second pieces into contact with each other in the absence of the interbody graft.

In an embodiment: the assembly is characterized by a longitudinal axis; the first piece further comprises a first transverse inclined surface; and the second piece further comprises a second transverse inclined surface generally parallel to the first inclined surface; and the first and second inclined surfaces are configured to urge the interbody graft at an angle relative to the longitudinal axis.

In an embodiment, the first body portion comprises a shoulder configured to abut a substantially flat surface of one of the anatomical structures.

A device is also provided for inserting a spacer between anatomical structures, the spacer having a bottom edge and a top surface. The device includes: first and second guides configured to move between a closed position and an extended position, at least one of the guides comprising a ramp; and an elastomeric component interconnecting the first and second guides; wherein, in response to a force applied to the top surface of the spacer: i) the bottom edge transmits a portion of the force to the ramp to thereby separate the first and second guides; and ii) the spacer is urged downwardly between the guides.

In an embodiment, the spacer comprises first and second bottom edges; the first and second guides comprises first and second ramps, respectively; and in response to force applied to the top surface of the spacer, the first bottom edge transmits a first portion of the force to the first ramp and the second bottom edge transmits a second portion of the force to the second ramp, causing the first and second guides to move away from each other.

In an embodiment, the first and second ramps generally define a funnel through which the spacer is passed.

In an embodiment, the elastomeric component is configured to return the first and second guides to a closed position after the spacer fully descends through the funnel.

In an embodiment, the device further includes a lock configured to releasably secure the device to an installation tool.

In an embodiment, the device is characterized by an axis and further includes a transverse internal surface configured to urge the spacer at an angle relative to the axis.

A method is also provided for installing a spacer between adjacent anatomical structures during a surgical procedure. The method includes: placing a guide assembly between the anatomical structures; pushing the spacer through the guide assembly to thereby simultaneously urge the adjacent anatomical structures apart and pass the spacer through the guide assembly; and removing the guide assembly following insertion of the spacer between the anatomical structures.

In an embodiment, the surgical procedure comprises a posterior lumbar interbody fusion; the spacer is an interbody graft device; and the anatomical structures comprise adjacent vertebrae.

In an embodiment, the method further includes: removing disc material from the space between the adjacent vertebrae; and packing the space with bone paste.

In an embodiment, the method further includes: acquiring a radiological image of an area surrounding the anatomical structures; and using the image to fabricate at least a portion of the guide assembly with a three dimensional printer to thereby custom fit the guide assembly to the patient's anatomy.

As used herein, the word "exemplary" means "serving as an example, instance, or illustration." Any implementation described herein as "exemplary" is not necessarily to be construed as preferred or advantageous over other implementations, nor is it intended to be construed as a model that must be literally duplicated.

While the foregoing detailed description will provide those skilled in the art with a convenient road map for implementing various embodiments of the invention, it should be appreciated that the particular embodiments described above are only examples, and are not intended to limit the scope, applicability, or configuration of the invention in any way. To the contrary, various changes may be made in the function and arrangement of elements described without departing from the scope of the invention.

The invention claimed is:

1. A system for use in a posterior interbody fusion procedure, the assembly comprising:

an interbody insert configured for fusing adjacent vertebrae, said interbody insert comprising a top surface and a bottom surface opposite to said top surface, a front surface and a back surface opposite to said front surface, and respective side surfaces opposite to each other, said surfaces are connected to each other forming the interbody insert;

a tool comprising an elongated shaft extending along a shaft longitudinal axis from a proximal end to a distal end, said shaft having a pair of tabs extending radially outward from said distal end;

a first sleeve piece extending along a first longitudinal axis from a proximal end to a distal end, said first sleeve piece having a first body portion and a first shank portion extending from the first body portion, a first internal ramp disposed within the first body portion, and a first circumferential groove portion formed in an outer surface of the first body portion, a first slot extending through the first shank configured for releasable engagement with one of the pair of tabs of the tool;

a second sleeve piece extending along a second longitudinal axis from a proximal end to a distal end, said second sleeve piece having a second body portion and a second shank portion extending from the second body portion, a second internal ramp disposed within the second body portion opposite the first internal ramp, and a second circumferential groove portion formed in an outer surface of the second body portion, a second slot extending through the second shank configured for releasable engagement with the other one of the pair of tabs of the tool;

each of the first and second shank portions having an outer surface and an inner surface, said inner surface defining an interior cavity having a base surface, and respective lateral surfaces for slidable engagement with one of the front surface and the back surface, and the respective side surfaces of the interbody insert;

wherein the first and second through slots extend through the inner and outer surfaces of the first and second shank portions, respectively; and an elastic band encircling the first and second sleeve pieces and disposed within the first and second groove portions, said elastic band configured to urge the first and second sleeve pieces towards each other in a low profile configuration;

wherein:

the first and second shank portions extend distally from and form a shoulder with the first and second body portions, respectively, such that the shoulders extend transversely to the first and second body portions and the first and second shank portions, and wherein the first and second shank portions are configured to be inserted between the adjacent vertebrae during the fusion procedure by the tool while the shoulders are configured to contact outer surfaces of the adjacent vertebrae to limit the insertion of the first and second shank portions between the adjacent vertebrae;

the first and second internal ramps slope inwardly from the proximal of the first and second sleeve pieces, respectively, to a distal portion of the respective body portion, such that the first and second internal ramps together form a V shape opening therebetween through which the interbody insert travels during the surgical procedure; and the first and second ramps are configured to urge the first and second pieces away from each other in an expanded configuration in response to downward force applied to the ramps by the interbody insert as an installation tool is urged downwardly against the top surface of the interbody insert pushing the interbody insert distally through the first and second sleeve pieces after the removal of the tool.

2. The system of claim 1, wherein the first and second pieces are configured to: i) mate with each other in the low profile configuration; and separate from each other in the expanded configuration.

3. The system of claim 1,
wherein the first and second shank portions comprise a combined width dimension in the range of 2 to 8 mm at the distal end of the first and second sleeve pieces.

* * * * *